United States Patent [19]
Kelleter et al.

[11] Patent Number: 5,668,304
[45] Date of Patent: Sep. 16, 1997

[54] APPARATUS FOR MEASURING A STATE VARIABLE IN A GAS WITH AT LEAST ONE SEMICONDUCTIVE GAS SENSOR

[75] Inventors: Jörg Kelleter; Claus-Dieter Kohl, both of Giessen; Heinz Petig, Essen, all of Germany

[73] Assignee: RWE Energie Aktiengesellschaft, Essen, Germany

[21] Appl. No.: 744,449

[22] Filed: Nov. 6, 1996

Related U.S. Application Data

[63] Continuation of Ser. No. 377,525, Jan. 20, 1995, abandoned.

[30] Foreign Application Priority Data

Jan. 20, 1994 [DE] Germany ............... 44 01 570.4

[51] Int. Cl.$^6$ ........................................... G01N 7/00
[52] U.S. Cl. ........................................... 73/31.05; 422/88
[58] Field of Search .................... 73/31.05, 31.06; 422/88, 98

[56] References Cited

U.S. PATENT DOCUMENTS

| | | | |
|---|---|---|---|
| 3,695,848 | 10/1972 | Taguchi | 23/254 E |
| 4,103,227 | 7/1978 | Zemel | 324/65 |
| 4,198,851 | 4/1980 | Janata | 73/23 |
| 4,234,542 | 11/1980 | Romine | 422/98 |
| 4,327,054 | 4/1982 | Yasuda et al. | 422/95 |
| 4,399,684 | 8/1983 | Advani et al. | 73/1 G |
| 4,638,443 | 1/1987 | Kaneyasu | 364/497 |
| 4,703,646 | 11/1987 | Müller et al. | 73/23 |
| 5,071,770 | 12/1991 | Kolesar | 436/151 |
| 5,143,696 | 9/1992 | Haas et al. | 422/90 |
| 5,202,637 | 4/1993 | Jones | 324/425 |
| 5,395,507 | 3/1995 | Aston et al. | 204/431 |
| 5,403,452 | 4/1995 | Hielscher et al. | 204/153.18 |
| 5,403,748 | 4/1995 | Pernisz | 436/113 |
| 5,431,883 | 7/1995 | Barraud | 422/82.01 |
| 5,448,905 | 9/1995 | Stetter | 73/31.05 |

OTHER PUBLICATIONS

Heiland & Kohl, "Interpretation Of Surface Phenomena On ZnO by the Composation Model" phys.stat.sol.(a)49,27 (1978) pp. 27–37.

*Primary Examiner*—Hezron E. Williams
*Assistant Examiner*—Jay I. Politzer
*Attorney, Agent, or Firm*—Herbert Dubno

[57] ABSTRACT

To eliminate the effects of semiconductive sensor aging in the use of a semiconductive sensor for measuring the state variables of a gas in a system in which a pair of electrodes are embedded in an active semiconductive layer so that the conductivity of the semiconductive layer varies as a function of the state variable, a field electrode is provided and superimposed upon the measurement voltage, a voltage pulse is applied intermittently and the characteristic of the resulting current pulse is used to compensate for changes resulting from aging of the sensor.

20 Claims, 3 Drawing Sheets ns, and proportions of the main components, changes in proportions and the like. Reference may be had to DE 43 21 736.2 A1 in this regard.

APPARATUS FOR MEASURING A STATE VARIABLE IN A GAS WITH AT LEAST ONE SEMICONDUCTIVE GAS SENSOR

CROSS REFERENCE TO RELATED APPLICATION

This is a file-wrapper continuation of application Ser. No. 08/377,525 filed Jan. 20, 1995 now abandoned.

FIELD OF THE INVENTION

Our present invention relates to an apparatus for measuring a state variable in gases with at least one semiconductive gas sensor and, more particularly, to an apparatus of this type in which the semiconductive gas sensor is connected in circuit with a power supply means and a measured-signal pickup or processor.

BACKGROUND OF THE INVENTION

The measurement of a state variable of a gas can be, in accordance with the invention, a quantitative measurement signalling a quantity of a gas or a proportion of a particular component in a gas or a qualitative measurement enabling a gas or combination of gases to be identified, or a monitoring of a gas for a change in a state variable or some identification of a particular state variable. Any combination of the foregoing types of measurements may be involved as well. A "state variable" as that term is used herein is intended to mean any thermodynamic parameter of a gas mixture or concentrations of the mixture components or combinations thereof and, for the purposes of the present application, the measurement of a state variable may also be said to include the detection of certain gases or certain levels of gas concentrations in a gas mixture or other environment.

Apparatus utilizing a semiconductive gas sensor, a power supply network in which the semiconductive gas sensor is connected and a measurement-signal processor or pickup responsive to the semiconductive gas sensor are known in a variety of forms. They can be constructed in various constructions and can be used for different purposes as will be apparent, for example, from German Utility Models G 91 13 607.5, G 93 09 638.0 and G 93 09 640.2, with the particular configuration being established with the end result and purposes in mind. The evaluation of the measurement signals can be effected by measuring temperature or other state variables of the gas by a comparison of two different states of the semiconductor gas sensor and from these measurements gas conditions and development patterns can be ascertained and compared with stored patterns to signal a particular condition or parameter of interest. The different states of the semiconductive gas sensor can be cyclically generated at the semiconductive gas sensor or the evaluation of the state of semiconductive gas sensor may be cyclically determined as desired or required.

Comparison can be effected between time-course evaluations of the semiconductive gas sensor output based upon recorded or stored values or patterns thereof, for example, after filtering of the output signals from the sensor, e.g. after low-pass filtering.

The comparison pattern may be determined by a calibration measurement from the measurement side or from some other source. Typical of the patterns which can be utilized are those which relate in general to composition determinations and proportions of the main components, changes in proportions and the like. Reference may be had to DE 43 21 736.2 A1 in this regard.

The semiconductive gas sensor can have a cover layer which is influenced by the gas and covering its entire surface or only part thereof and is affected especially by diffusion of oxidizing or other gases in metal oxides (DE 43 21 736.2 A1).

The physics of the relationship of the various surface phenomenon of such a device is developed in Phys. Stat. Sol. (a) 49, 27 ff. (1978).

Commercially available semiconductive gas sensors based upon metal oxides such as $SnO_2$, $WO_3$, $Fe_2O_3$ and $In_2O_3$ are available as are those which are based upon organic compounds, for example, phthalocyanines or pyroles. The choice of the sensor used for a particular purpose will depend, of course, on the measurements to be made and the particular characteristics of the sensor.

In the conventional devices over which the invention represents an improvement, the semiconductive gas sensor has an insulating layer and a conductor structure on one side of this insulating layer and an active semiconductive layer thereon in which the two electrodes are embedded in spaced relationship. The conductor structure can form part of a heating circuit which enables the operating temperature of the semiconductive gas sensor to be set. It is known to operate such a sensor with a pulsed or nonpulsed operating voltage, obtaining pulsed or nonpulsed measurement voltages and thus to provide one or more pulse-voltage generators in the circuit arrangement.

Experience has shown that the earlier device is susceptible to long-term stability problems, especially with reference to the zero point of the sensor. Indeed, a high degree of variability and fluctuations in the zero point are found. The long-term stability does depend upon the fabrication techniques as well as upon the specific operating conditions and can be influenced by the choice of working temperature, by the repetition frequency of the temperature fluctuations and by the gas components and their concentration fluctuations. The sensitivity of the semiconductive gas sensor varies, e.g. as a result of changing morphology, as variations in concentrations of catalytically active components of the gas, by adsorption of catalytically active substances, by irreversible adsorption of gases which tend to form highly stable solid compounds, and the like. These effects can render a semiconductive gas sensor more or less unusable after even a brief operating period.

As a consequence, the improvement of known devices for the purposes described so that the semiconductive gas sensors are more reliable and more precise with greater long-term stability, has been highly desirable.

To avoid the quality falloff, it has hitherto been the practice to recalibrate the semiconductive gas sensors with a standardization or test gas after more or less short operating intervals. That, of course, is expensive.

OBJECTS OF THE INVENTION

It is, therefore, the principal object of the present invention to provide an improved apparatus for measuring one or more state variables in a gas with at least one semiconductive gas sensor whereby functional reliability is enhanced and the need for repeated and frequent recalibration is eliminated.

It is also an important object of this invention to provide an improved apparatus for the purposes described which will be free from many of the drawbacks detailed above.

SUMMARY OF THE INVENTION

These objects and others which will become apparent hereinafter are attained, in an apparatus for the measurement of a state variable in gases having at least one semiconductive sensor in circuit with a power supply network and a measurement-signal processor, wherein:

(a) the semiconductive gas sensor has an insulating layer and, on the insulating layer, a field electrode as well as two spaced-apart further electrodes, (b) the two further electrodes are embedded in an active semiconductive layer while the field electrode is insulated or isolated from the semiconductive layer and the further electrodes thereof, and (c) A pulse-voltage generator is connected on the one hand to the field electrode and on the other to at least one of the further electrodes embedded in the semiconductive layer. According to the invention, moreover, measurement of the state parameter is effected by determining the conductivity of the active semiconductive layer via the further electrodes and, in addition, for autogenous monitoring of the function of the semiconductive gas sensor, at time-spaced intervals, pulses are applied by the pulse-voltage generator between the field electrode and one of the embedded further electrodes and the conductivity reading of the semiconductive layer is measured as a function of time via the measurement signal processing system.

In other words the apparatus for measuring a state variable in a gas can comprise:

a semiconductive gas sensor disposed in a gas having a state variable to be monitored, the semiconductive gas sensor comprising:

an insulating layer, a field electrode on the insulating layer, an active semiconductor layer on the insulating layer and spaced by the insulating layer from the field electrode, and two spaced apart further electrodes embedded in the semiconductor layer and isolated from the field electrode;

a power supply connected in circuit with the further electrodes;

a measurement-signal processor connected in circuit with the power supply and the further electrodes of the semiconductive gas sensor for detecting a signal across the semiconductive gas sensor representing conductivity of the semiconductive layer and the state variable; and a voltage-pulse generator connected across the field electrode and at least one of the further electrodes for applying time-spaced pulses between the field electrode and the one of the further electrodes for autogenous control of sensor functioning by generating conductivity changes in the semiconductive layer as a function of time which are measured by the measurement-signal processor.

The invention is based upon the recognition that control of the function of a semiconductive gas sensor is possible when a field electrode is additionally provided as described and the semiconductive gas sensor is operated in the manner set forth, i.e. with periodic pulsing. Thus in addition to the conductivity measurement for the purpose of detecting the state variable, an autogenous function control of the semiconductive gas sensor is carried out in time-spaced intervals by superimposing on the sensor the described voltage pulse.

The apparatus of the invention can be provided in various configurations and constructions. For example, in one embodiment, the semiconductive gas sensor has on one side of the insulating layer, the two further electrodes as well as the active semiconductive layer while on the opposite side of the insulating layer, the field electrode is provided.

Alternatively, in another embodiment, on one side of the insulating layer, the two electrodes and semiconductive layer are disposed and, separate from the latter, the field electrode is provided on the same side of the insulating layer. In this case a covering glass insulating layer can separate the field electrode from the active semiconductive layer in which the further electrodes are embedded. The glass insulator can cover the field electrode. A conductive structure can be provided on the insulating layer, in addition to the field electrode but insulated therefrom, for connection to a heating circuit.

The insulating layer can be a thin layer with a thickness of 30 to 100 nm which can be composed, for example, of silicon oxide and/or silicon nitride and/or aluminum oxide.

The conductive structure can be composed of highly conductive metal or of polysilicon. With the invention it has been found to be advantageous to provide the field electrode so that at the applied voltage (for the voltage pulses) the maximum possible field strength can be obtained without breakdown of the insulation. Preferably the field electrode should be capable of generating field strengths in the range of $10^4$ to $10^6$ V/cm. The power supply can be designed to apply an operating voltage of about 10 volts or even less.

For control of the measuring process and to evaluate the measurement result, advantageously the circuit arrangement comprises a microcontroller. The microcontroller can also be utilized to ascertain the conductivity between the further electrodes and can function as the measurement signal processor as well as the monitoring device for the autogenic function monitoring of the sensor. In accordance with the invention, the operating temperature of the semiconductive gas sensor is adjusted in critical measurement ranges by the use of the heating circuit. The operation of the active semiconductive gas sensor can be effected with direct voltage although it is also possible to operate the active semiconductive gas sensor with pulsed direct voltage.

As a theoretical explanation, it can be presumed that the gas or gas component whose state variable is measured or whose presence is detected generates either donors or acceptors which raise or lower the charge carrier density in the active semiconductive layer. The result is a change in conductivity between the embedded electrodes which serves as a sensor signal allowing determination of the state variable, e.g. the gas concentration. At each surface of the semiconductive layer, a portion of this charge concentrates at so-called accumulation locations. The strong electric fields which are applied in pulses in accordance with the invention through the use of the field electrodes, change the charge density in these accumulation regions and in the semiconductive layer. When the pulsed field is turned off, the original charge distribution is restored. Because of the morphology of the surface and irreversibly bound gases, a spectrum of accumulation regions can form which take up or release charge carriers in a field strength change at different rates. As a consequence of these effects, patterns which are typical of aging of the semiconductive gas sensor can be largely eliminated from affecting the evaluation even over extended periods of time.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
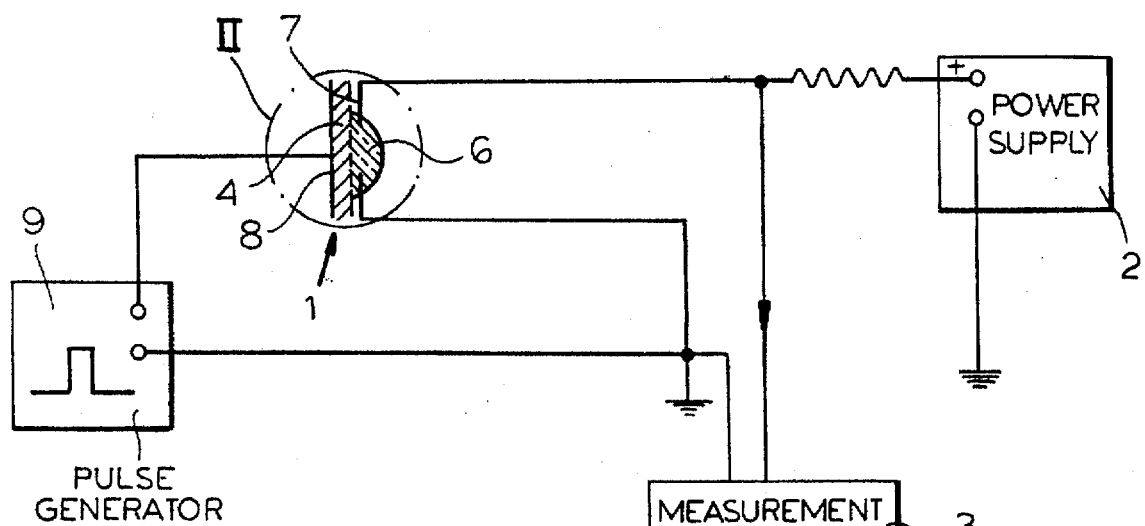
FIG. 1 is a diagram of a system according to the invention in accordance with a first embodiment.
Figure 2:
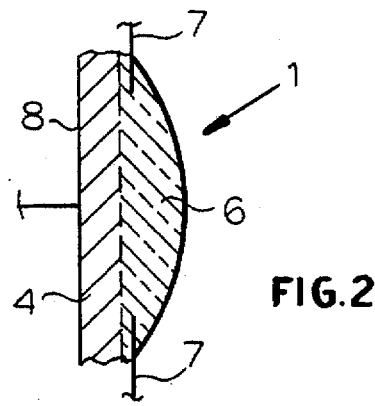
FIG. 2 is a detail of the construction of the sensor of FIG. 1 drawn to a larger scale.
Figure 4:
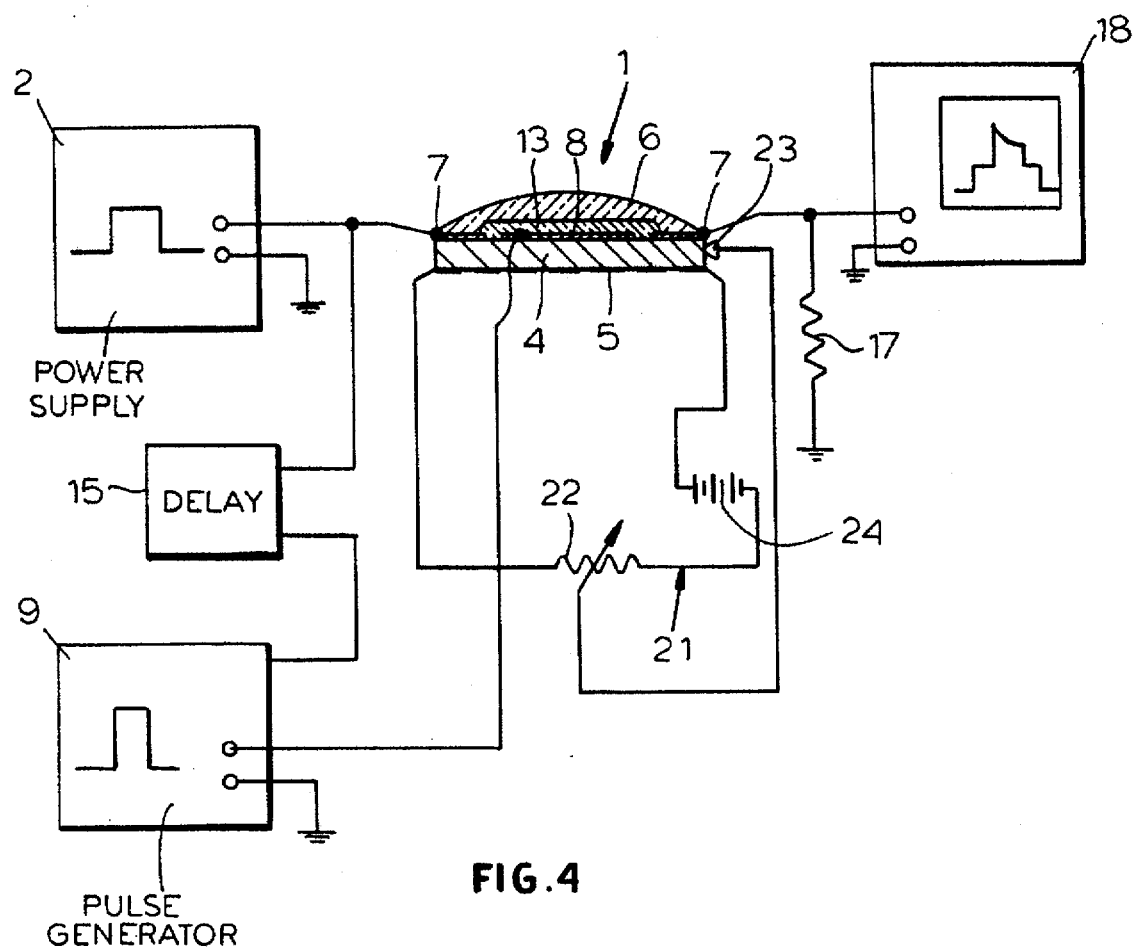
FIG. 4 is a circuit diagram of another apparatus in accordance with the invention.
Figure 5:
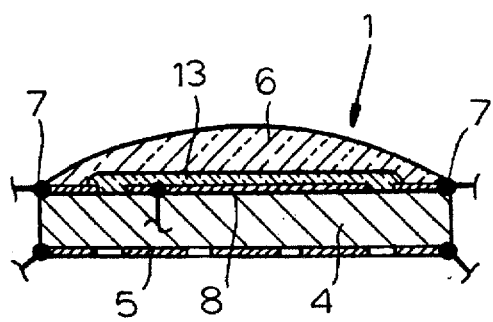
FIG. 5 is a cross sectional view through the semiconductor sensor thereof drawn to a larger scale.

The devices as shown in FIGS. 1 and 2 on the one hand and in FIGS. 4 and 5 on the other serve for the measurement of state variables in gases, e.g. the concentration of one gas component in a gas mixture, say carbon monoxide in the ordinary atmosphere, and comprise for this purpose at least one semiconductive gas sensor 1.

The gas sensor 1 is connected in circuit with a power supply 2 or other network capable of supplying the sensor with any requisite electric current, and a measurement signal pickup or detector 3. In the embodiment of FIGS. 1 and 2, the semiconductive sensor comprises an insulating layer 4 constituting a substrate on one side of which a field electrode 8 is provided while on the opposite side two spaced-apart electrodes 7 are disposed.

The two electrodes 7 are embedded in an active semiconductive layer 6, the field electrode being insulated from the semiconductive layer 6 and from the electrodes 7 by the insulating substrate 4. A pulse-voltage generator 9 is connected between the field electrode 8 and one of the electrodes 7 embedded in the semiconductive layer 6. In the embodiment of FIGS. 1 and 2, to which the measurement trace of FIG. 3 generated by a pen recorded display 20 belongs, the semiconductive gas sensor 1 is provided on one side of the insulating layer 4 with the two electrodes 7 and the active semiconductive layer 6 while the field electrode 8 is provided on the opposite side of the insulating layer 4.

To carry out a measurement of the state variable in a gaseous environment, the semiconductive gas sensor of FIGS. 1 and 2 is introduced into the gas or the gas is admitted to the presence of the semiconductive gas sensor. The measurement of the state variable is effected by measuring the conductivity of the active semiconductive layer 6 between two electrodes 7.

Figure 3:
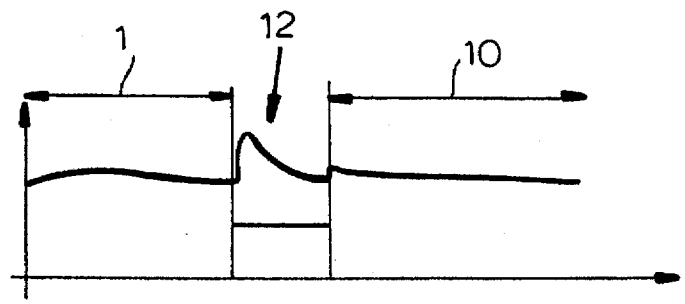
FIG. 3 is a diagram of the measurement result with time as plotted on a pen recorder.

FIG. 3 shows the change in conductivity over time in the constant-voltage regions 10. The recorder trace is generated by a microcontroller 11 from the signal supplied thereto by the pickup 3. In addition, autogenous function control of the semiconductive gas sensor is ensured by applying pulses from the pulse generator 9 in time-spaced intervals, e.g. periodically, between the field electrode 8 and one of the electrodes 7 embedded in the semiconductive layer 6. The application of such pulses, e.g. square wave pulses as has been shown in FIG. 1, results in a conductivity change which is superimposed upon the the constant voltage and has been illustrated in FIG. 3 as a positive pulse 12 which rises rapidly and practically spikes, but decays substantially more slowly.

This peak 12 contains information as to the aging status of the semiconductive gas sensor as will be developed in greater detail below. The peak 12 and its decay can be compared with a calibration pattern or stored patterns representing the aging states of the sensor.

The embodiment of FIGS. 4 and 5 differs from that of FIGS. 1 and 2 in that the two electrodes 7 are provided directly upon the insulating layer or substrate 4 and on the same side thereof as the field electrode 8 but are insulated from the field electrode 8 by an insulating layer 13, e.g. of nonconductive glass. The semiconductive active layer 6 is applied over the electrodes 7 and the glass insulating layer so that the latter insulates the field electrode 8 also from the semiconductive layer.

On the opposite side of the insulating layer or support 4, a conductor structure 5, e.g. a grid, is provided which can be connected in a heating circuit 21 provided with a control element 22, such as a potentiometer which responds to a temperature sensor 23 at the insulating layer 4 allowing feedback control of the temperature of the semiconductive sensor.

The circuitry in FIG. 4 can include the power supply 2 or power network which is connected to one of the embedded electrodes 7 and ground while the pickup of the measurement signal is here tapped across the resistor 17 in series with the sensor by an oscillograph 18.

The voltage pulse for control of the sensor aging is supplied by the pulse generator 9 connected between the field electrode 8 and ground and hence between the field electrode and the embedded electrode 7 connected with the resistor 17. A delay network 15 is also provided and has a function as will be described.

The operation of the system of FIGS. 4 and 5 will best be understood together with FIGS. 6–9 showing waveforms which will be considered as if they are displayed upon the oscillograph 18.

The semiconductive gas sensor 1 is heated to a constant temperature by the heating circuit 21 which includes a source of heating current 24 and the temperature control network 22, 23.

The operating voltage (a constant voltage of say 10 volts as described) for measurement of the current through the stretch of the semiconductive layer 6 between the electrodes 7 is supplied by the network 2 and may be supplied in the form of measurement pulses periodically. To that extent we may refer here to the measurement pulses 14.

With a delay of say 5 ms after switching on of the operating voltage, under the control of the delay line 15, a voltage pulse with a duration of 10 ms can be applied between the field electrode 8 and one of the electrodes 7 to produce a field pulse 16. The pulse generator 9 may be capable of delivering square wave pulses with a level of say 50 volts.

In this manner, a field with a field strength of about $5\times10^3$ V/cm can be generated. The current amplitude through the active semiconductive layer 6 is measured as a voltage drop across the series connected resistor 17 which is smaller by at least an order of magnitude than the resistance of the semiconductive layer 6. The signal displayed in FIG. 4 is that which is obtained in the measurement of the carbon monoxide concentration in a gas stream passing over the semiconductive gas sensor.

If the time dependency of the current is displayed on an oscillograph during application of a measurement pulse 14 and the superimposed field pulse 16, the curves shown in FIGS. 6–9 are obtained.

Figure 6:
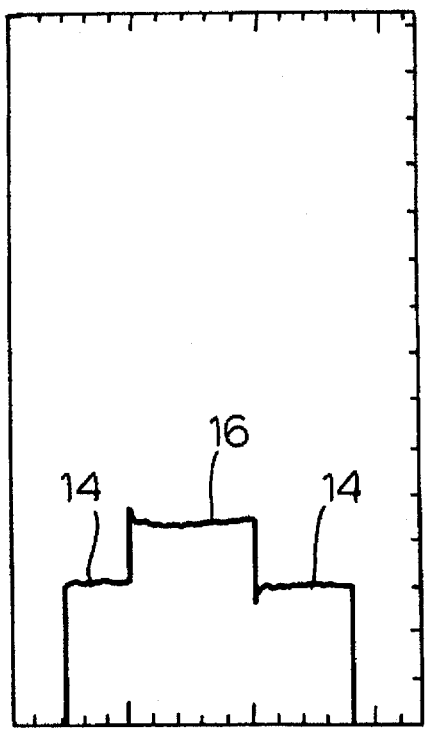
FIGS. 6–9 are waveform diagrams showing measurement results and corresponding generally to that of FIG. 3 but under the conditions of the invention.

FIG. 6 shows the current response to the pulses 14, 16 with a freshly prepared semiconductive gas sensor according to the invention in air and without the presence of carbon monoxide.

Figure 7:
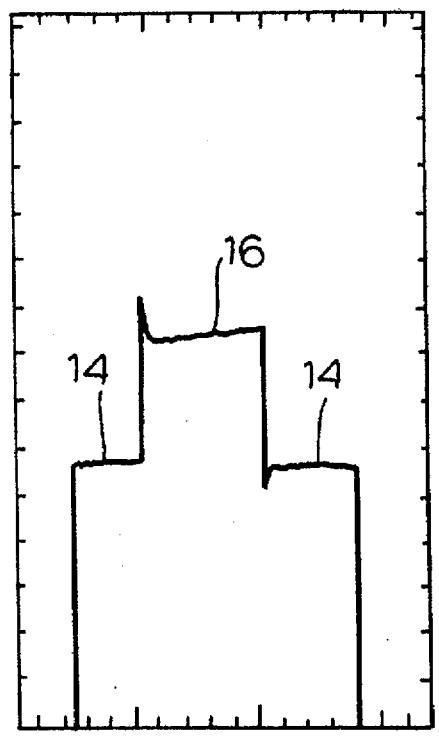

FIG. 7 shows the current response with the same freshly prepared semiconductive gas sensor in the presence of 20 ppm carbon monoxide. By comparison to FIG. 6, while there are differences in level representing the presence of the carbon monoxide, the ratio of the pulse heights and the shape thereof do not change materially. The current amplitude in the current response for the measurement pulse 14 has, as a consequence of the lower resistance of the semiconductive sensor 1 in the presence of carbon monoxide, increased.

Figure 8:
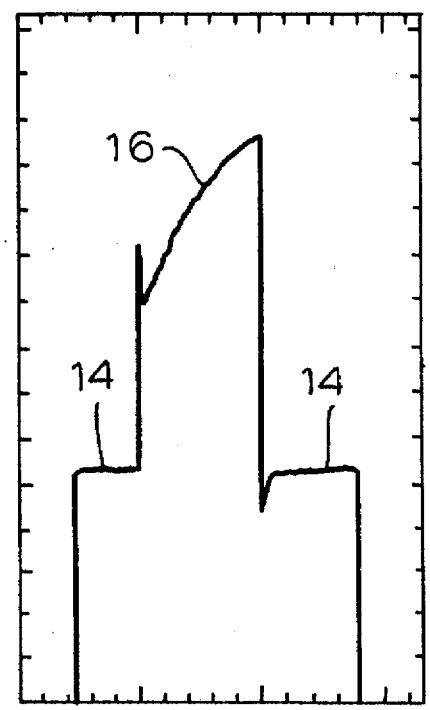

FIG. 8 shows the current response with the same semiconductive gas sensor after aging, measured in air in the absence of carbon monoxide. By comparison to FIG. 6 the pulse amplitudes are substantially greater, signifying that the resistance of the semiconductive layer has lowered as a consequence of aging. If, therefore, the aging characteristics of the sensor 1 were not considered and only the levels of the current pulses were used as an indication of the measurement of the carbon monoxide content, the results would have been falsified as a consequence of the aging. Utilizing the difference in the pulse shapes and height ratios from FIG. 6–FIG. 8, the microcontroller 11 and the microprocessor incorporated into the oscillograph 18 can be programmed to recalibrate the sensor for the aging characteristics thereof as detected periodically by the application of the field pulses.

Figure 9:
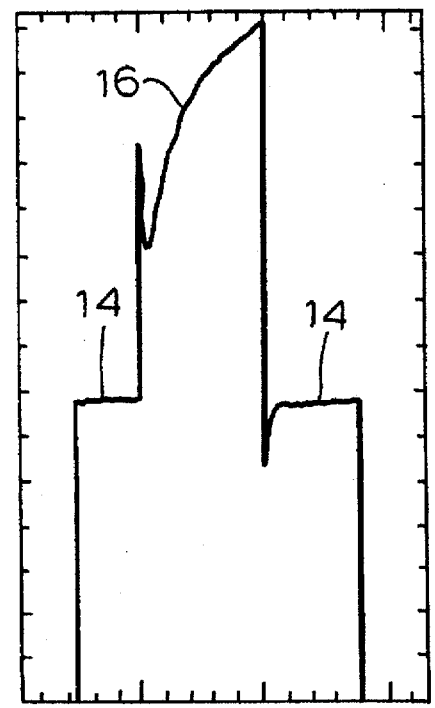

As a comparison of FIGS. 8 and 9 will show, FIG. 9 representing the current responses of the aged semiconductive sensor in the presence of 20 ppm carbon monoxide, a characteristic of the aging process which can be used as a measure of aging, is the rise time of the current during the application of the field volts 16, the field pulse current reaching its maximum only toward the end of its pulse duration. The rise of the current during the current pulse 16 after several ms following triggering of the pulse can then be used as a representation, measure of the aging of the sensor for the calibration. As a result of the recalibration, the pulses can be evaluated cyclically to compensate for the aging of the sensor that the carbon monoxide concentration can be read out without falsification as a result of sensor aging.

We claim:

1. An apparatus for measuring a state variable in a gas, comprising:
 a semiconductive gas sensor disposed in a gas having a state variable to be monitored, said semiconductive gas sensor comprising:
 an insulating layer,
 a field electrode on said insulating layer,
 an active semiconductor layer on said insulating layer and spaced by said insulating layer from said field electrode, and
 two spaced apart further electrodes embedded in said semiconductor layer and isolated from said field electrode;
 a power supply connected in circuit with said further electrodes;
 a measurement-signal processor connected in circuit with said power supply and said further electrodes of said semiconductive gas sensor for detecting a signal across said semiconductive gas sensor representing conductivity of said semiconductive layer and said state variable;
 a voltage-pulse generator connected across said field electrode and at least one of said further electrodes for applying time-spaced measurement pulses between said field electrode and said one of said further electrodes for autogenous control of sensor functioning by generating conductivity changes in said semiconductive layer as a function of time which are measured by said measurement-signal processor for each of said pulses; and
 means responsive to the measurement pulses for superimposing upon each of said measurement pulses a respective second measurement signal which is modified by aging of the semiconductive layer.

2. The apparatus defined in claim 1 wherein said semiconductive layer and said further electrodes are disposed one side of said insulating layer, and said field electrode is disposed on an opposite side of said insulating layer.

3. The apparatus defined in claim 1 wherein said field electrode, said semiconductive layer and said further electrodes are disposed on one side of said insulating layer, a covering glass insulating layer is applied to said field electrode to insulate said field electrode from said semiconductive layer.

4. The apparatus defined in claim 1, further comprising a conductor structure on said insulating layer connectable in a heating circuit for resistive heating of said sensor.

5. The apparatus defined in claim 1 wherein said insulating layer is a thin layer of a thickness of 30 to 100 nm.

6. The apparatus defined in claim 1 wherein said insulating layer is composed of silicon dioxide, silicon nitride, aluminum oxide or mixtures thereof.

7. The apparatus defined in claim 4, wherein said conductor structure is composed of a highly conductive metal or doped polysilicon.

8. The apparatus defined in claim 1 wherein said voltage pulse generator is constructed and arranged to generate a field strength of $10^4$ to $10^6$ V/cm.

9. The apparatus defined in claim 1 wherein said power supply is constructed and arranged to apply a voltage of about 10 V across said further electrodes.

10. The apparatus defined in claim 1, further comprising a microcontroller connected to said power supply and said generator for controlling progress of a measurement of a state variable and autogenous function control.

11. The apparatus defined in claim 1 wherein, for operation at a critical measuring range of the active semiconductive sensor, said sensor has a heating structure thereon connectable to a heating circuit.

12. The apparatus defined in claim 1 wherein said sensor is operated with direct current or with periodically applied direct current.

13. The apparatus defined in claim 10, further comprising a conductor structure on said insulating layer connectable in a heating circuit for resistive heating of said sensor.

14. The apparatus defined in claim 13 wherein said insulating layer is a thin layer of a thickness of 30 to 100 nm.

15. The apparatus defined in claim 14 wherein said insulating layer is composed of silicon dioxide, silicon nitride, aluminum oxide or mixtures thereof.

16. The apparatus defined in claim 15, wherein said conductor structure is composed of a highly conductive metal or doped polysilicon.

17. The apparatus defined in claim 1 wherein said voltage pulse generator is constructed and arranged to generate a field strength of $10^4$ to $10^6$ V/cm and said power supply is constructed and arranged to apply a voltage of about 10 V across said further electrodes.

18. The apparatus defined in claim 17 wherein said semiconductive layer and said further electrodes are disposed on one side of said insulating layer, and said field electrode is disposed on an opposite side of said insulating layer.

19. The apparatus defined in claim 18 wherein said field electrode, said semiconductive layer and said further electrodes are disposed on one side of said insulating layer, a covering glass insulating layer is applied to said field electrode to insulate said field electrode from said semiconductive layer.

20. In a method of measuring a state variable in a gas with an apparatus which comprises:

a semiconductive gas sensor disposed in a gas having a state variable to be monitored, said semiconductive gas sensor comprising:

an insulating layer, a field electrode on said insulating layer, an active semiconductor layer on said insulating layer and spaced by said insulating layer from said field electrode, and two spaced apart further electrodes embedded in said semiconductor layer and isolated from said field electrode;

a power supply connected in circuit with said further electrodes;

a measurement-signal processor connected in circuit with said power supply and said further electrodes of said semiconductive gas sensor for detecting a signal across said semiconductive gas sensor representing conductivity of said semiconductive layer and said state variable;

a voltage-pulse generator connected across said field electrode and at least one of said further electrodes for applying time-spaced measurement pulses between said field electrode and said one of said further electrodes for autogenous control of sensor functioning by generating conductivity changes in said semiconductive layer as a function of time which are measured by said measurement-signal processor, the improvement which comprises the steps of:

generating for each of said measurement pulses a respective second measurement signal, superimposing each second measurement signal upon the respective measurement pulse, each second measurement signal being modifiable in response to aging of the semiconductive layer, and evaluating a change in a rise time of said second measurement signal for each of said measurement pulses as a function of aging.

* * * * *